United States Patent [19]
Chen

[11] Patent Number: 6,033,283
[45] Date of Patent: *Mar. 7, 2000

[54] HUMDINGER, STRING SPINNING TOY

[75] Inventor: John Youngfu Chen, Pacifica, Calif.

[73] Assignee: Applied Elastomerics, Inc., South San Francisco, Calif.

[ * ] Notice: This patent is subject to a terminal disclaimer.

[21] Appl. No.: 08/211,781

[22] PCT Filed: Apr. 19, 1994

[86] PCT No.: PCT/US94/04278

§ 371 Date: May 14, 1996

§ 102(e) Date: May 14, 1996

[87] PCT Pub. No.: WO95/13851

PCT Pub. Date: May 26, 1995

Related U.S. Application Data

[63] Continuation-in-part of application No. 08/152,734, Nov. 15, 1993, Pat. No. 5,624,294, and application No. 08/114,688, Aug. 30, 1993, Pat. No. 5,475,890, and application No. 07/935,540, Aug. 24, 1992, Pat. No. 5,336,708, and application No. 07/876,118, Apr. 29, 1992, Pat. No. 5,324,222, and application No. 07/705,096, May 23, 1991, Pat. No. 5,655,947, which is a continuation-in-part of application No. 07/527,085, May 21, 1990, and application No. 07/957,290, Oct. 6, 1992, Pat. No. 5,334,646, and application No. 07/705,711, May 23, 1991, Pat. No. 5,262,468, which is a continuation-in-part of application No. 07/211,426, Jun. 24, 1988, Pat. No. 5,153,254, which is a continuation-in-part of application No. 06/921,752, Oct. 21, 1986.

[51] Int. Cl.[7] .............................. A63H 1/32; A63H 33/00
[52] U.S. Cl. ......................... 446/253; 446/254; 446/486
[58] Field of Search ................................ 446/46, 48, 74, 446/253, 254, 486; 482/110, 121, 122

[56] References Cited

U.S. PATENT DOCUMENTS

| | | | |
|---|---|---|---|
| 2,988,846 | 6/1961 | Samuel | 46/62 |
| 3,069,162 | 12/1962 | Samuel | 272/79 |
| 3,131,506 | 5/1964 | Fox | 46/63 |
| 3,269,727 | 8/1966 | Samuel | 272/79 |
| 3,672,094 | 6/1972 | Vigorito | 46/62 |
| 3,789,545 | 2/1974 | Mann | 46/62 |
| 4,003,575 | 1/1977 | Hobbs | 272/68 |
| 4,369,284 | 1/1983 | Chen | 524/476 |
| 4,846,757 | 7/1989 | McMurray | 446/486 |
| 4,953,854 | 9/1990 | Pizur, Sr. | 272/93 |
| 5,399,136 | 3/1995 | Bart | 482/110 |
| 5,512,028 | 4/1996 | Sparks, III | 482/92 |
| 5,624,294 | 4/1997 | Chen | 446/253 |

*Primary Examiner*—Paul J. Hirsch
*Assistant Examiner*—Michael B. Priddy

[57] ABSTRACT

Dynamic, spinning, twisting string toys referred to as "humdingers" are disclosed. The toys include at least one highly elastic gel body having at least two holes extending through the body along a selected axis of rotation. The holes are treaded with a string(s) which are twisted and untwisted alternatively by the pulling and releasing action of the strings. The holes are provided with means to resist the shearing forces of the twisting strings. The dynamic effect of the extreme high centrifugal and shearing forces generated during play causes the gel bodies to change shape during spinning. Soft gels or low strength materials can also be substituted in place of the highly elastic gel body provide the body reinforced with shear resistant means to prevent cutting by the twisting and untwisting actions of the string(s).

15 Claims, 4 Drawing Sheets

HUMDINGER, STRING SPINNING TOY

ORIGINS OF INVENTION AND RELATED APPLICATIONS

This application is a continuation-in-part application of copending applications Ser. No. 152,734, filed Nov. 15, 1993; Ser. No. 114.688, filed Aug. 30, 1993; Ser. No. 935,540 filed Aug. 24, 1992; Ser. No. 876,118 filed Apr. 29, 1992; Ser. No. 705,096 filed May 23, 1991 (which are continuation-in-part applications of Ser. No. 527,085 filed May 21, 1990); Ser. No. 957,290 filed Oct. 6, 1992; and Ser. No. 705,711 filed May 23, 1991 and issued as U.S. Pat. No. 5,262,468 on Nov. 16, 1993 which is a continuation-in-part application of Ser. No. 211,426 filed Jun. 24, 1988 and issued as U.S. Pat. No. 5,153,254 on Oct. 6, 1992 which is a continuation-in-part application of Ser. No. 921,752 filed Oct. 21, 1986. The subject matter contained in the related applications and patents are specifically incorporated herein by reference.

BACKGROUND OF THE INVENTION

1. Technical Field of invention

The present invention relates to string spinning toys.

2. Background of Art

A spinning toy made of narrow thin film strips or fins of durable plastic film, taped to a central hard plastic support cylinder with two holes therethrough for spinning on a string is available from Rainbow Products of Trail, Oreg. under the tradename "ORBITER". The ORBITER transforms the nearly straight film strips on both sides of the rigid spinning cylinder into two side lobs by the action of centrifugal force. Another string spinning toy available from Giggles Toy Co., Inc., of MT. Clemens, Mich. is described in U.S. Pat. No. 4,986,790 and tradenamed the "WILD THINGS". It consist of two rigid plastic cylinders with two holes suspended on a string for spinning.

Historically, string spinning toys have been around for a long time. in the nineteenth and early Twentieth centuries, various rigid, hard, materials such as shells, wood, bones, metals, ceramics, ivory, glass, rigid plastics, ect were used to make buttons. The large buttons with their well placed center holes 6 made them ideal for spinning on strings. In the Eighteen century, large copper pennies were commonly use by children for spinning on a string. These were called "humdingers". The word "humdinger" has since lost its meaning. Today, the word refers to anything that is extraordinary.

It is certain that string spinning toys date back to much earlier times and were enjoyed by many cultures, possibly before recorded history. From the earliest tires to the present, all known string spinning toys utilize a hard structural support with bores or holes. One major disadvantage of spinning toys with hard surfaces is that the string breaks often and requires replacing. No prior art is known to exist that require solutions to problems which are only inherent and unique to the string spinning toys of the present invention.

DISCLOSURE OF INVENTION

Statement of Invention

I have unexpectedly discovered novel string spinning toys and methods of making and using comprising highly elastic gel bodies which are deformed and elongated by the centrifugal force of rotation generated by the dynamic twisting actions of the strings. The invention is also directed to string spinning toys comprising bodies made from materials having low strength which can easily be cut through by the dynamic twisting actions of the string.

For want of a simpler name to call them, I will hereinafter define, describe, claim and in all respects refer to the string spinning toys of my invention as "humdingers".

The preferred embodiments of the string spinning toys of the invention comprises a highly elastic gel body having at least two holes at a selected distance apart and extending through said body along a selected axis of rotation, said body suspended by a selected length of a string(s) having ends, said string formed in a loop through said holes with said ends tied together to provide for alternatively clockwise and counterclockwise rotation of said body by the twisting and untwisting of said string, said body being deformed and elongated by the action of centrifugal force of rotation of said body, and said body having sufficient strengths to withstand the centrifugal force of rotation and shearing force of the twisting and untwisting of said string generated by a first, a second, a third, or higher order dynamic twisting of said string during spinning.

Another preferred embodiment of the string spinning toys of the invention comprises a body made from a low strength material having at least two holes at a selected distance apart and extending through said body along a selected axis of rotation, and a selected length of two or more shear resistant tubes inserted into said holes and positioned within said body, said body suspended by a selected length of a string(s) having ends, said string formed in a loop threaded through said tubes residing within said holes with said ends tied together to provide for alternatively clockwise and counterclockwise rotation of said body by the twisting and untwisting of said string, said body being deformed and elongated by the action of centrifugal force of rotation of said body, and said body having sufficient strengths to withstand the centrifugal force of rotation and said tubes having sufficient strengths to withstand the shearing force of the twisting and untwisting of said string generated by a first, a second, a third, or higher order dynamic twisting of said string during spinning.

Still another preferred embodiment of the string spinning toys of the invention comprises a soft, highly elastic gel body having at least two holes at a selected distance apart and extending through said body along a selected axis of rotation, and a selected length of two or more shear resistant tubes inserted into said holes and positioned within said body, said body suspended by a selected length of a string having two ends, said string formed in a loop threaded through said tubes residing within said holes with said ends tied together to provide for alternatively clockwise and counterclockwise rotation of said body by the twisting and untwisting of said string, said body being deformed and elongated by the action of centrifugal force of rotation of said body, and said body having sufficient strengths to withstand the centrifugal force of rotation and said tubes having sufficient strengths to withstand the shearing force of the twisting and untwisting of said string generated by a first, a second, a third, or higher order dynamic twisting of said string during spinning.

A broadly preferred embodiment of the string spinning toys of the invention comprises a soft, highly elastic gel body or a body made from a low strength material having at least two holes at a selected distance apart and extending through said body along a selected axis of rotation, and a shear resistant means inserted within or surround said holes, said body suspended by a selected length of a string(s)

having ends, said string formed in a loop threaded through said shear resistant means within or surround said holes with said ends tied together to provide for alternatively clockwise and counterclockwise rotation of said body by the twisting and untwisting of said string, said body being deformed and elongated by the action of centrifugal force of rotation of said body, and said body having sufficient strengths to withstand the centrifugal force of rotation and said shear resistant means having sufficient strengths to withstand the shearing force of the twisting and untwisting of said string generated by a first, a second, a third, or higher order dynamic twisting of said string during spinning.

Specifically, the shear resistant means of the present invention which surround said holes comprises a reinforced interlocking material region, one or more shear resistant tubes, or a shear resistant gel region, said gel region surrounding said holes having a gel rigidity of at least about 600 gram Bloom.

The present invention also describes a method of rotating a body comprising forming an elastic gel body or a body of low strength material having a selected shape, a selected volume, a selected surface, and at least two holes substantially parallel and approximately equal distance along a selected axis of rotation through said volume of said body; said holes optionally having a shear resistant means inserted within or surround said holes; threading into said holes of said body a selective length of a string(s) having ends; optionally, said string(s) having two or more holding means for holding said string(s); tiding said ends of said string(s) together forming a string loop communicating through said holes of said body; suspending said body by said string(s); holding said string by said holding means; twirling said body about said string(s) followed by pulling and relaxing said string(s) so as to cause a continue twisting and untwisting actions of said string loop and the rotation of said gel body thereby deforming said volume of said gel body by the centrifugal force of rotation; said twisting and untwisting actions is capable of generating a first, a second, a third, or higher order dynamic twisting of said string during spinning.

The various aspects and advantages of the humdingers of the invention will become apparent to those skilled in the art upon consideration of the accompanying disclosure and the drawings.

FIGURES

FIG. 1. Representative sectional views of various humdingers.

FIG. 2. Representative sectional views of more humdingers.

FIG. 3. Representative sectional views of additional humdingers.

FIG. 4. Representative sectional views of strings with end handles.

MODES FOR CARRYING OUT THE INVENTION

The preferred humdingers of the invention comprises one or more highly elastic bodies or a single body 2 having two or more holes 6 substantially equal distance apart extending through the body 2 transversely along a selected axis of rotation of the body 2. The holes 6 are threaded through with a suitable length of string(s) 5 forming a loop with the ends of the string(s) 5 tied together which string(s) 5 are dynamically twisted and untwisted alternatively in play.

The body 2 may be formed from a strong shear resistant gel having one or more holes 6. Each of the holes 6 of the body 2 may be fitted or molded in placed with shear resistant moans (e.g. tubes 8) for preventing cutting by the shear forces or the twisting string(s) 5. Where the body is formed from a less shear resistant gel, the the holes 6 may be surrounded with a strong shear resistant gel to prevent cutting by the twisting string(s) 5. Furthermore, the body 2 may be formed with holes 6 which are surrounded by an reinforcing interlocking material 9 interlocked with the body 2. Where the body 2 contains three or more holes 6, the corresponding numbers of strings 5 are threaded though each of the holes 6 are tied together at opposite ends.

Figure 4A:
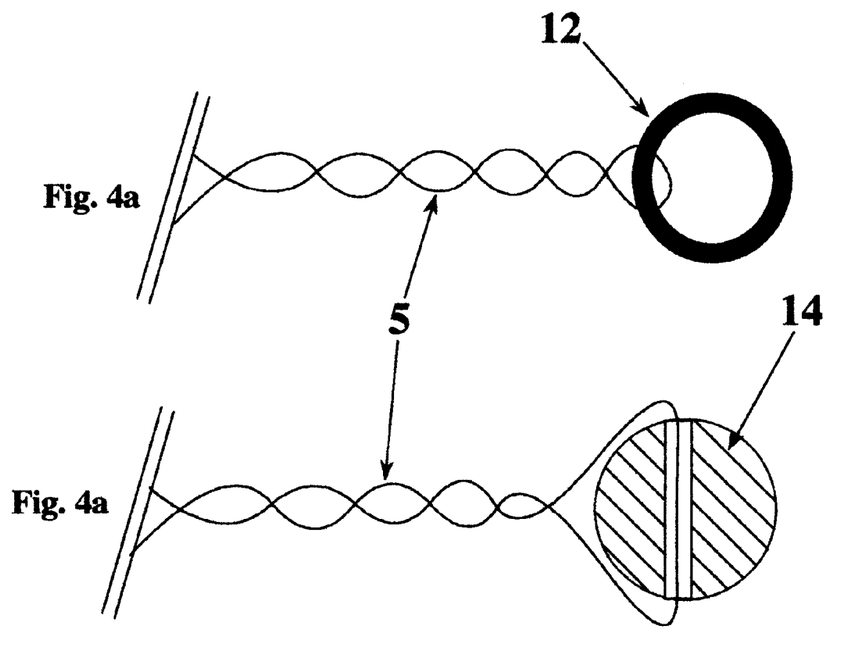
Figure 4B:
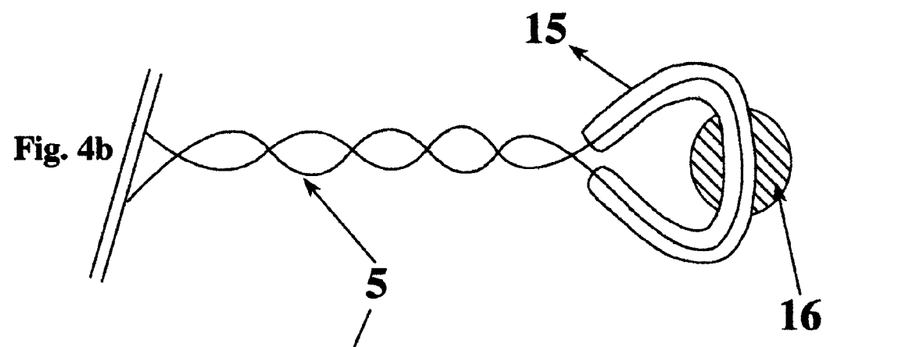
Figure 4C:
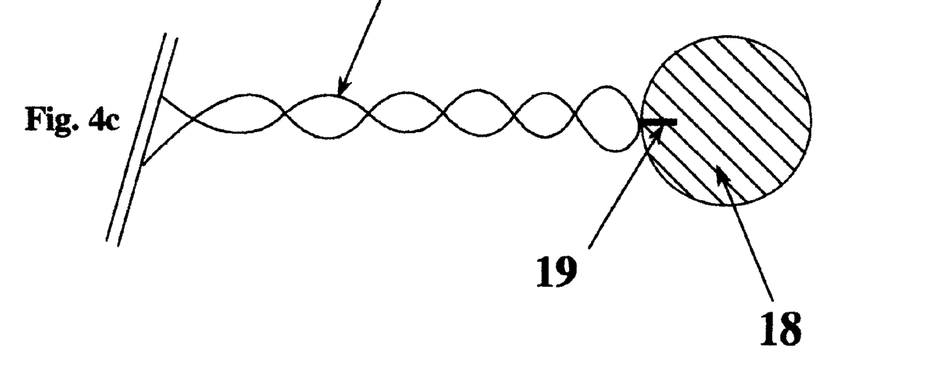

In the operation of the humdingers, the body 2, the the shear resistant means (e.g. the tubes 8, the interlocking materials 9 surrounding the holes, etc), and the string(s) 5 are selected so that they do not result in disastrously effects caused by the extreme conditions generated during play. The string 5 ends may be threaded with suitable handles, such as: rings 12, nobs (14, 16, 18), tubing 15, combinations thereof (15, 16), and the like for holding the string(s) 5 while spinning the body 2.

Although the preferred bodies 2 of the invention are made of strong and highly elastic gels which can resist the shearing forces generated by the twisting strings, other materials useful in making the bodies 2 include low strength materials (foams, rubber uncure gums, soft gels, very soft gels, weak gels, etc.) which can be cut by the dynamic shearing forces of the twisting strings 5.

For purpose of the present invention, low strength materials are defined as those materials which can be cut by the forces generated by the twisting action of the strings 5. The magnitude of the forces of concern are those generated by one or more strings 5 or pairs of dynamically twisting strings 5 (under a first, second, third, or higher order twisting action). The term dynamic twisting strings 5 refers to two or more strings 5 twisted or bundled together undergoing alternating twisting action. For example: a first order twisted pair of strings 5 can generate an inward pull of at least one pound force and greater, a second order twisted pair of strings 5 can generate a pull of at least three pound force and greater, and a third order twisted pair of strings 5 can generate a pull of at least five pound force and greater, etc.

When a gel body 2 is set into rotation of at least 100 r.p.m. (revolutions per minute) to as high as 1,000 r.p.m. and higher, the forces can be significant. The following examples can best illustrate the forces involve.

The inward pulling forces generated by a pair of twisting stings 5 as measured on a spring scale for a 2.00" (5.08 mm) dia.×0.50" (12.70 mm) thickness spinning circular gel body 2 can range from an extreme of less than one pound to forty pounds and greater. The typical range for such a spinning gel body 2 may range from between less than five pounds to twenty pounds and greater. As another example, the measured pulling forces for a (smaller) 1.75" (44.46 mm) dia.×0.60" (15.24 mm) spinning circular gel body 2 can range from an extreme of less than one pound to twenty five pounds and greater. The typical range for such a smaller body 2 is between less than three pounds to about eight pounds and greater.

For the purpose of the invention, an indirect measure of the shearing forces generated during play is measured (in lbs) by the inward pulling forces of the twisting strings 5 on a spring balance during dynamic spinning. The typical values can range from less than one pound to fifty pounds and greater. String puling forces for various shapes (large and small) of spinning bodies 2 having measured values of 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 . . . 40, 50, 60, 70, 80 pounds and greater can be achieved and such values are typical. During spinning, the measured pulling force is read as a dynamic measurement which starts from a low value and rise as the string(s) are pulled apart forcing the body to reaching a maximum spin rate (i.e. maximum measured pulling force value).

The problems associated with the spinning of bodies 2 made from highly elastic gels, and various low strength materials and the means of solving such problems are specifically detailed below.

The dynamic variables due to the centrifugal force of rotation of the bodies 2, such as, elongation, stress and shear forces, under extreme high torque conditions, and the accelerations and deaccelerations involved are ever changing during play. A humdinger made without consideration to such variables may not be able to synchronize under high rates of rotation. In order for the humdingers of the invention to operate in substantial synchrony and exhibit stability, these variables must be taken into account in the design, selection of materials, and the bodies' 2 proper construction. The undesirable effects include: instability, uncontrollable chaotic behavior, damping out of the driving force, lack of synchronization, extreme sensitivity to initial conditions of play, fibrillations, and the like. Due to the highly elastic nature of the preferred bodies 2, the bodies 2 are deformed by the centrifugal force as the rate of rotation is increased. The inherent disorder and instability associated with an elastic body 2 are not encountered with rigid materials used in conventional toys which utilizes hard structures.

The bodies 2 of the humdingers of the invention can be view as semi-elastic liquids. They are highly elastic and dynamically deformable under rotation (see FIG. 3. g' deforms to h' and d' deforms to c'). Since the bodies 2 are highly elastic, they are easily deformed under very low to moderate shear and stress forces; and therefore, are not suitable for use as gyroscopes which require high rigidity.

Figure 1A:
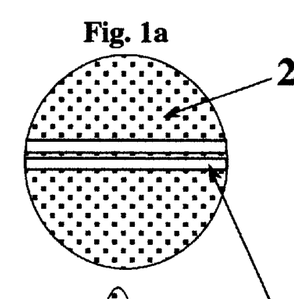
Figure 1B:
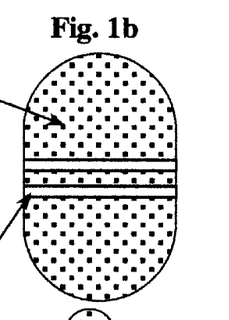
Figure 1C:
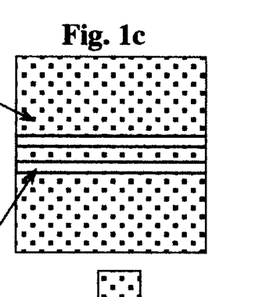
Figure 1D:
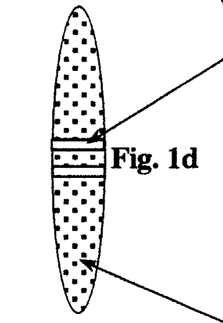
Figure 1E:
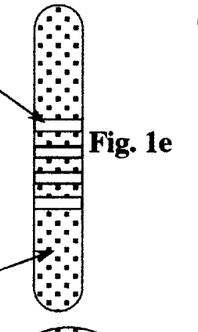
Figure 1F:
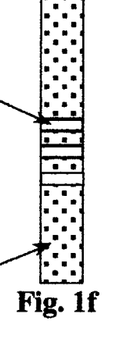
Figure 1G:
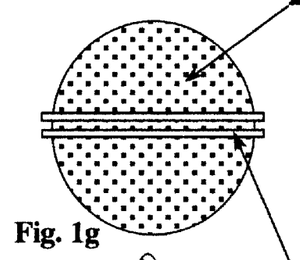
Figure 1H:
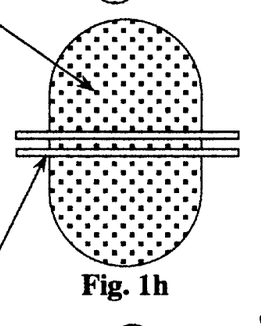
Figure 1I:
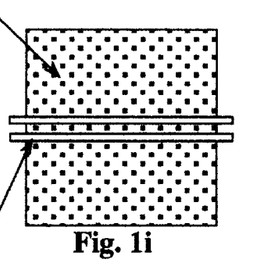
Figure 1J:
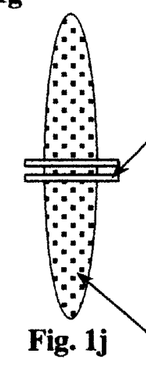
Figure 1K:
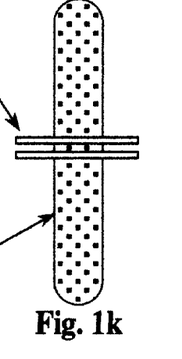
Figure 1M:
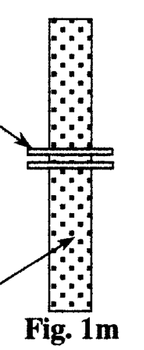
Figures 2A, 2B, 2C, 2D, 2E, 2F, 2G, 2H, 2I, 2J, 2K, 2M, 2N:
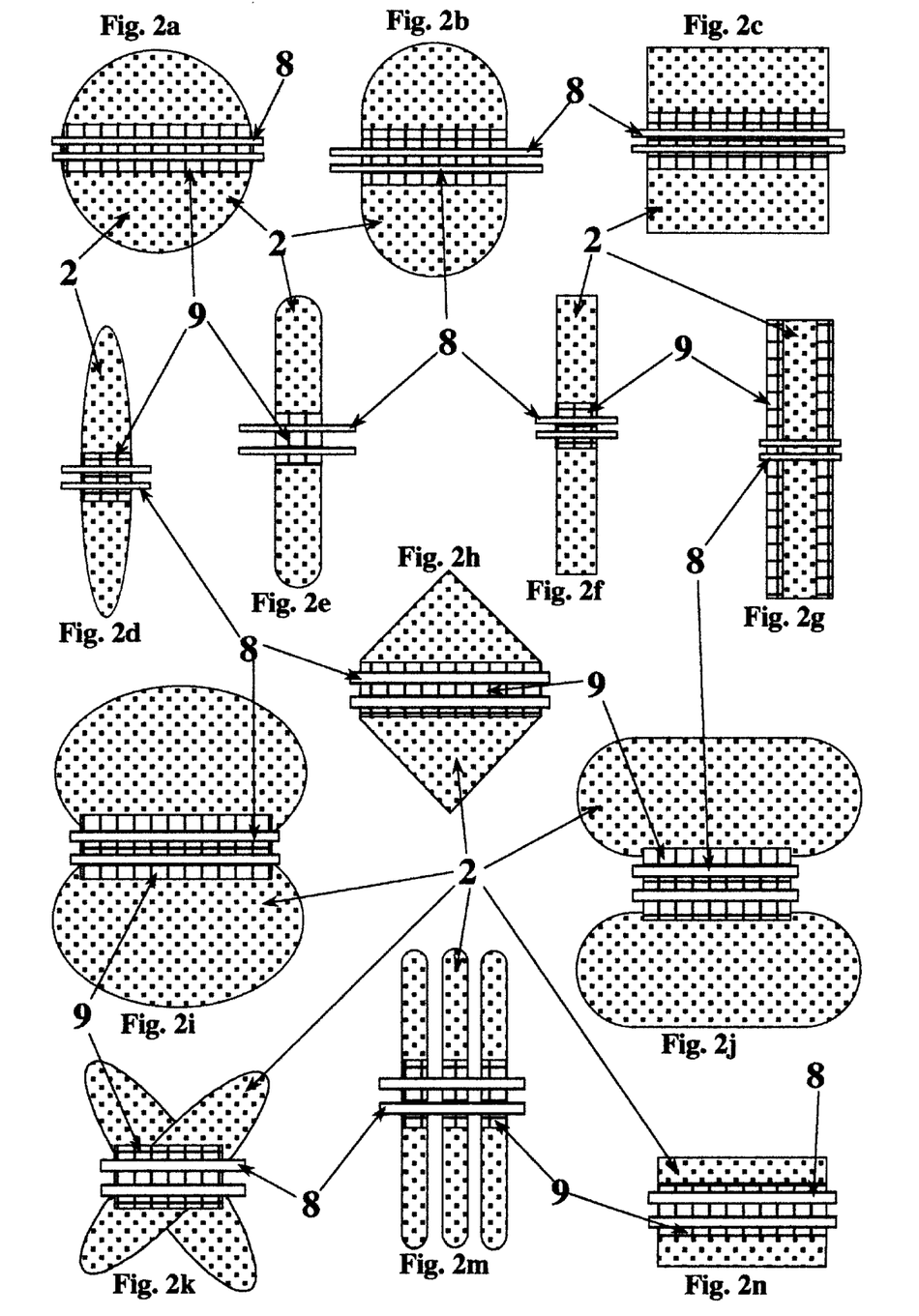
Figures 3A, 3B, 3C, 3D, 3E, 3F, 3G, 3H, 3I, 3J, 3K, 3M:
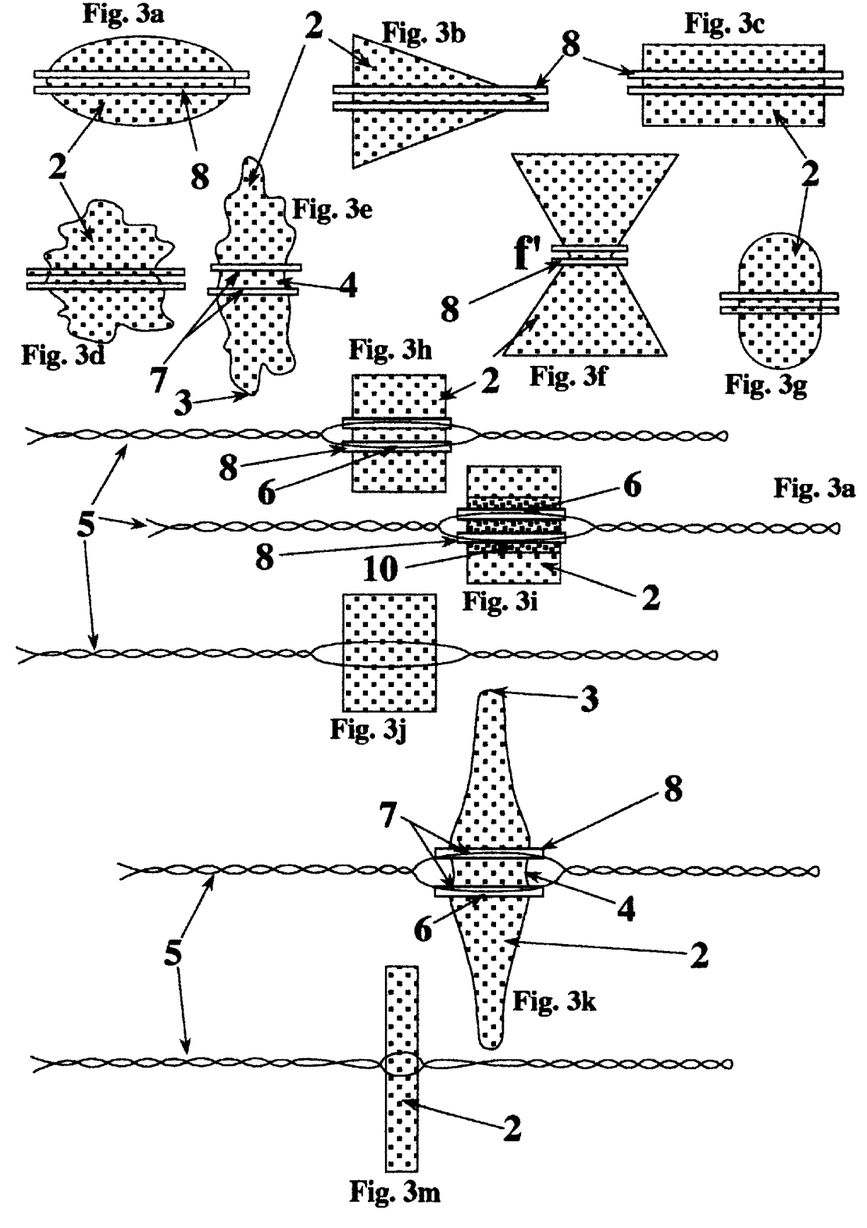

The bodies 2 of the invention when rotated about an axis of rotation will experience increase deformation from its original shapes with increase rate of rotation (e.g. see FIG. 3, c' and h'). Irrespective of the original shapes of the bodies 2, when subjected to rotational forces, the bodies 2 will deform in a highly elastic, predetermined, nonuniform, and non-radial manner. Because of the high deformations resulting from rotational forces, the bodies 2 will distribute its mass outwardly by elongating perpendicularly with respect to its axis of rotation (so FIG. 3. c' and h'). The gel material at the extreme outer parts 3 (equator) of the bodies 2 will experience greater and greater centrifugal force as the bodies 2 rotate and elongate more and more. The bodies 2 if not properly designed will be pulled apart by the increasing centrifugal force of rotation. For example, the centrifugal force of a rotating body 2 having a mass of about 50 grams and an elongated mass about the body's equator of about 10 centimeter may produce from less than about 50 to about 250 pound-force or higher.

As described herein above, the humdingers of the invention comprises one or more bodies 2 suspended on a inner looped string 5. The bodies 2 are made with two or more holes 6 parallel about their axis of rotation. The holes 6 are positioned approximately equal distance apart about the axis of rotation of the bodies 2 and may pass through the bodies' 2 center of mass, but at some selected distance form it or the holes 6 may pass through the bodies' 2 center of suspension (suspended from a line passing through its center of mass, i.e. at neutral equilibrium) but at some selected distance form it. This is to say, one hole is placed above the center of mass line, the body 2 is in stable equilibrium; and the other hole 6 is placed below the line, in unstable equilibrium. Such positioning of the holes 6 with respect to the center of mass (the center of weight) or the center of suspension will provide the desired torque need to maintain adequate rotation imparted by the twisting string(s) 5.

If the hole 6 separation distance is zero, then the torque will also be zero. Therefore, a suitable separation distance is needed to separate the holes 6 from each other and the holes 6 from the selected axis of rotation. The holes 6 should be separated approximately equal distance from the axis of rotation. A suitable distance, x, may be selected based on various factors, including the moment of inertia, axis of rotation, and the necessary torque need to rotate the bodies 2 about its axis of rotation by the action of the twisting string 5. If the separations between the holes 6 with respect to the axis of rotation is slightly off, then the torque applied to the bodies 2 will be unbalanced. The unbalanced rotation would not be totally disastrous, but may produce a desirable off-balanced effect. While the humdinger may still adequately operate, it will be more difficult to keep the wobbling humdinger rotating in the unbalanced state.

As the bodies 2 rotate, the moment of inertia will change and the point of the applied torque will also change (see FIG. 3. c'/7 and h'/7). The moment of inertia of the bodies 2 changes because the shape of the bodies 2 changes (e.g. FIG. 3. d' is transformed to c' and g' is transformed to h') with increase rate of rotation. Due to the highly elastic nature of the gel bodies 2, as their shape change, so will the position of the holes 6 with respect to each other and with respect to their distances from the axis of rotation. Any off-centering of the placement of the holes 6 with respect to the axis of rotation will be greatly magnified by the centrifugal force acting on the body 2, since the original placement of the holes 6 will also be changed due to elastic stretching. The torque acting on the bodies 2 will greatly vary as the centrifugal force further separates the holes 6 from each other and from the axis of rotation (see FIG. 3, c'/4 and h'/4).

Moreover, the over all original shape of a body 2 will also affect the position of the holes 6 as the body 2 is set into rotation. The change in separations between the holes 6 and the change in distance between the holes 6 and the axis of rotation due to the centrifugal force acting on the body 2 is also affected by the shape of the original body 2 as a whole. In other words, the configuration of the original shape of the elastic body 2 directly affects the amount and direction of the elastic deformation about the holes 6 caused by the centrifugal force. A stretching or elastic deformation of one part of a body 2 will directly affect other parts of the body 2 as well. Therefore, any deformation by an applied force on any part of the body 2 will correspondingly cause deformation to other parts of the body 2. The holes 6 and the shape of the bodies 2 are always in a state of flux due to the forces generated during rotation. The holes 6 freely move about as the shape of the body 2 is changed by the force of rotation. This is the nature of bodies 2 (i.e. semi-elastic liquids) under dynamic motion as opposed to rigid bodies.

The shape of the bodies 2 of the humdingers of the invention may be of any suitable solid shape, such as a sphere, a hemisphere, a spherical triangle, a spherical segment, a spherical sector, a curved volume of a right cylinder, a curved volume of a right cone, an oblate spheroid, an oblate hemispheroid, a semi-hemispheroid, a quai-hemispheriod, a prolate, a spheroid, a prolated hemispheroid, a frustum of right circular cone, a solid lune, or an ellipsoid, and the like.

Other shapes of bodies 2 of the humdingers of the invention include: a cube, a rectangular solid, a parallelogram solid, a rhombus solid, a trapezoid solid, a general quadrilateral solid, a rectangular parallelepiped, a prism, a truncated triangular prism, a pyramid, a frustum of pyramid, a bifolium solid, an evolute solid, a lemniscate of Bernoulli, two-leaved rose solid, a nephroid solid, a three-leaved rose curve solid, a four-leaved rose curve solid, an elliptic paraboloid, a hyperbolic paraboloid, a hyperboloid, a tetrahedron, an octahedron, an icosahedron, a dodecahedron, an ellipsoid, a spheroid, an oblate spheroid, or a prolate spheroid, and the like. Tubular shaped bodies, hollow shaped bodies, or solid shaped bodies 2 with bubbles, voids, inclusions (various thin, solid or liquid objects) can also be used.

Any suitable axis of rotation of the bodies 2 may be chosen as the axis of rotation. The bodies 2 may be of any suitable size, from less than 1 cubic centimeter to 20 cubic centimeter or greater.

Suitable strings 5 suspending the bodies 2 may have a test strength of less than one pound to 100 pound or greater. Strings 5 of sufficient test strengths of less than about 10 to 15, 20, 25, 30, 50, 60, 70, 80, 90 pounds and greater may be used depending on the size, weight, axis of rotation, and inertia of the gel bodies 2 and the rate of rotation. The breaking strength of the string 5 should be greater that the force required to operate the humdingers at the designed maximum spinning speeds.

The construction of the strings 5 can be solid braid, hollow braid, double braid, maypole braid, twisted, and the like. The material of the strings 5 can be natural or synthetic, such as: manila, sisal, cotton, nylon, polyester, polypropylene, polyethylene, Kevar®, Spectra®, and the like.

The string 5 is passed through the two holes 6 of the gel body 2 and tied into a loop. For gel bodies 2 having three or more holes 6, the individual strings 5 may be passed through the holes 6 and tied together at opposite ends. The gel body 2 is set into continuous alternating rotating motion with an initial twirl of the body 2 followed by alternately pulling and releasing the string 5 while holding it in opposite directions which keeps it spinning. Between the second and fourth full reversal of rotation of the gel body 2, the string 5 will had sufficient twist to shear off, cut into or through the gel material separating the holes 6. Gel material of low strength can not resist the tremendous shearing action of the twisting strings 5 between the holes 6. The twisting action of the strings 5 generated by the spinning gel body 2 can exhibit a first order twist, a second order twist, or higher order twists. A first order twist refers to one or more twists of a pair of strings 5 (i.e. a pair of strings 5 when twisted together forms a small tight binding helix). A second order twist refers to one or more large binding helixes build up by a pair of strings 5 that have been twisted beyond the maximum number of twist which normally produce small tight binding helixes of the first order kind. Similarly, a third order twist refers to a much larger tightly binding helix build up by the maximum number of second order twists produced by the pair of twisting strings 5. The third order twist may be manifested by the appearance of a branch of two or more twist of the first order twisting strings 5.

In order to better demostrate the different type of order twist states, the same type of twisting can be observed in the twisting of a long rubber band held in place on a rubber band powered propeller toy airplane. The order of twisting will increase (from a one, two, three, and higher order twist) until the rubber band breaks. Likewise, a looped string with one end attached to a spring scale and the other end attached to a fixed anchor can be twisted into a first, second, third, and higher ordered twist state. This method will directly measure the force generated for each ordered twist states. The static force generated by twisting a string on a spring scale is the same due to the force generated in the twisting of the strings 5.

The shear force created by the static twisting of the string 5, however, is substantially different than the shear force generated under dynamic twisting of the strings 5. This can be demostrated by taking a sample of any of the soft gel bodies 2 and subject it to static twisting between a pair of strings under a static spring load of 20, 30, and 40 lbs for twenty four hours and compare the condition of the sample to samples of the same gel body subject under dynamic twist spring load of less than 20 lbs. (e.g. 5, 8, 10, 12, 16, 18, etc.). The results show that the shear force produce by a dynamic twist spring load of less than 20 lbs will easily cut a soft gel body or any low strength material body while the same sample will remain substantially uncut under a higher static twist spring load. Therefore, it is important to take into consideration the drastic effects of the shear force produced by the dynamic twisting of a pair of strings.

Suitable interlocking materials 9 (that help resist the shear force of the twisting strings 5) for use in the humdingers of the invention include: open cell foams, other polymeric or elastomeric (Kraton) materials, porous materials, multi-layered coatings, single layered, composite layered materials. As an example, an opened cell foam when dipped into the instant composition will form an interpenetrating physical networks (interlocking of gel composition and foam composite). Such composite will exhibit greater rigidity and resistance to the shear force generated by the a first, a second, a third, or higher order dynamic twisting of a pair of strings 5.

Furthermore, the interlocking materials 9 surrounding the holes 6 of the gel bodies 2 may be made from flexible materials, such as fibers and fabrics of cotton, flax, and silk. Other flexible materials include: elastomers, fiber-reinforced composites, mohair, and wool. Useful synthetic fibers include: acetate, acrylic, aremid, glass, modacrylic polyethylene, nylon, olefin, polyester, rayon, spandex, carbon, sufar, polybenzimidazole, and combinations of the above. Useful open-cell plastics include: polyamides, polyimides, polyesters, polyisocyanurates, polyisocyanates, polyurethanes, poly(vinyl alcohol), etc. Open-celled Plastic (foams) suitable for use with the compositions of the invention are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference. These include: open and non-opened cell silicone, polyurethane, polyethylene, neoprene, polyvinyl chloride, polyimide, metal, ceramic, polyether, polyester, polystyrene, polypropylene. Example of such foams are: Thanol®, Arcol®, Ugipol®, Arcel®, Arpak®, Arpro®, Arsan®, Dylite®, Dytherm®, Styrofoam®, Trymer®, Dow Ethafoam®, Ensolite®, Scotfoam®, Pyrell®, Volana®, Trocellen®, Minicel®, and the like.

Additionally, a preferred embodiment of the invention which would adequately resist the shearing force of the twisting string 5 is to provide a suitable length of tubing for insertion into the passage of the holes 6. Such a tube 8 may be made from a high strength tubing material. The tube 8 may be made from a rigid, flexible, or elastic material. The tube 8 may be smooth, treaded, ribbed, porous or roughly surfaced; it may be of any suitable hollow shape, round, square, rectangular, oval, and the like. The tubes 8 may be inserted into the holes 6 mechanically or by hand. The length of the tube 8 should be at least equal to the thickness portion of the gel body 2 which is being suspended by the string 5. The diameter of the tube 8 should be sufficient to receive the selected size of the string 5 passing through it without being too tight or too loose. The diameter of the tube 8 may be less than 1/16" to 1/4" and greater. The thickness of the tube 8 may be less than 1/32" to 1/8" or greater. A ribbed flange (not shown) may be incorporated (as a securing device) at the ends of the tube 8 to further secure the tube 8 within the holes 6 of the gel body 2. The securing device may also be constructed of a two coupled flanges (not shown) which inserts on to both tubes 8 at each ends keeping the separations of the holes 6 and tubes 8 at a fixed distance apart and securing the tubes 8 inside the holes 6 of the gel body 2 during the humdinger's operation. In this way the applied torque can be set at a fixed distance apart. On the otherhand, if the tubes 8 are joined at a fixed distance apart, the stretching of the gel body 2 during high speed spinning will further induce additional stress in the bodies 2 at the location of the holes 6 and ultimately tear at the holes 6 and in time destroy the gel body 2. It is more preferable for the tubes 8 residing in the holes 6 to remain independently deformable, flexible, and free to move with the stretching of the gel body 2. The tubes 8 can be bonded to the walls of the holes 6 or tightly pressure fitted into the holes 6 and held in place by friction. For a well balanced spinning body 2 the friction between the gel and tube 8 is adequate to keep the tube 8 positioned in place.

Tubing material suitable for use in the present invention include such high strength materials as: liquid crystal polymer, polyamide, polybutylene terephthalate, polyetherimide, polyarylsulfone, polyethylene terephthalate, polyacetal, polyphenylene sulfide, polysulfone, alkyd polyester, epoxy, phenolic, urea formaldehyde, polypropylene, polymethyl methacrylate, acetal copolymer, nylon, tetrafluoroethylene, chlorotrifuoroethylene, polyvinylidene fluoride, high density polyethylene, ethylene-vinyl acetate, ethylene-ethyl acrylate, ethylene-methyl acrylate, polystyrene, polyvinyl chlorides, acrylonitrile butadiene styrene, chlorinated polyether, cellulose acetate butyrate, polypropylene, polycarbonate, polyphenylene oxide, phenolic plastics, furane plastics, polyester, neoprene rubber, nitrile rubber, certain silicone rubbers, chorosulfonated polyethylene, fluoroelatomers, polyvinyl chloride elastomers, wood, glass, metal, polysulfide, SIS, SBS, SEBS, SEPS, SEPS/SEP, SEPS/SEP/SEBS, and the like. Various materials, metals, including thermoplastic materials such as thermoplastic elastomers, polyethylene, polypropylene, polybutylene, thermoplastic urethanes, ethyl vinyl acetate, nylon, polyester, and the like car be heat treated to bond to the holes 6 of the humdingers of the invention.

The tubing materials useful in the invention typically have hardness (of less and greater values) as determined by ASTM D785 and D2240: 64A, 73A, 75A, 92A, 36D, 44D, 65D, 70R, 78R, 96R, and 119R; elongations ASTM D882 and D638: 200, 300, 350, 400, 450, 500, 700, and greater; tensile strength, psi: 200, 500, 800, 1000, 1230, 2000, 2100, 2300, 2800, 3800, 6.3×103, 7.5×103, and higher. The tubing material can be made clear, milky, semi-opaque, or in different colors.

A gel having rigidities of about 800 to 1,500 gram Bloom and higher are sufficiently suited to substantially resist the shearing actions of the dynamic twisting strings 5. Such strong elastic gel 10 (i.e., resistant to the cutting actions of the twisting string 5) are most suitable for use in surrounding the holes 6 of the gel bodies 2. The higher strength gel 10 will have sufficient resistance for protecting the holes 6 of the gel bodies 2. Less preferably, the gels with rigidities of about 300 to about 1,500 gram Bloom and higher are suitable for use as gel bodies 2 without any additional need for any reinforcing, interlocking material 9 or tube 8 to protect the holes 6 against cutting by the twisting string 5. With respect to gel bodies 2 made from gels having rigidities in the range of about 750 to about 1,500 and higher, these are especially preferred for use as humdingers of the invention.

The holes 6 of the gel bodies 2 may be preformed by molding, casting, or any manner of forming the gel bodies 2. Higher rigidity gels may be utilized to surround the holes 6 of softer gel bodies 2, while lower gel rigidities may be use to advantage for the outer portion of the gel bodies 2 surrounding the holes 6. For example, a first high strength gel 10 of rigidity of about 300 to about 1,500 gram Bloom may be used to cast the central portion of the gel body 2 forming the holes 6 and a second gel of about 100 to 500 gram Bloom or lower may be used to mold the portion of the gel body 2 surrounding the holes 6. The holes 6 may be moled in place, punched-out, cut, or pierced using a knitting needle. With respect to gel bodies 2 made from higher strength gels 10, the string 5 may be treaded through the gel body 2 by simply piercing and tying the ends of the string 5 and it is then ready for play. A knitting needle if properly driven into the gel and withdrawn will leave very little trace of its penetration into the gel body 2. Two or more holes 6 may also be driven into the gel body 2 by insertion of the tubes 8. In forming the holes 6, the holes 6 should be properly aligned substantially parallel and spaced apart about the selected axis along the line of the center of mass. The preformed holes 6 in the gel body 2 may be made small enough to provide a tight fit for the tubes 8. The preformed holes 6 may be made small enough or suitably channeled inside with ribs or contours to provide a substantial tight fit around the tubes 8. Likewise, the gel bodies 2 may be casted with the tubes 8 in place.

Gel bodies 2 having certain extended shapes, such as a rectangular solid, a parallelogram, a rectangular parallelepiped, a cylinder, and the like can suitably be string 5 tied about their middle or girth for rotation. For such gel bodies 2, holes 6 may be used, but are not the only means to affect spinning of the bodies 2. The ability to hold a gel body 2 (in place) around the girth or middle circumference requires tying the gel body 2 with sufficient "pinch" so as to resist the gel body 2 from slipping through the tying string 5 loop (k'). During spinning, the gel bodies 2 tend to stretch out and reduce their middle circumference allowing the gel body 2 to slip through the string 5 loop. It is found that a 20% to 50% circumference reduction can sufficiently prevent the string 5 loop from slipping through. The string 5 loop can be readily tied around the gel body's girth by first stretching the body 2 and tying the string 5 while the gel body 2 is in the stretched state. This works very well for bodies 2 made from strong gels having sufficient strength to prevent the string 5 from cutting into the gel body 2 around the girth.

The bodies 2 of the humdingers of the invention can be made from any gel material with suitable elastic properties. These include: (1) Memory-gel®, (2) various polymer gels; (3) crosslinked polymer gels; other less suitable gels include high strength: (4) silicone gel; (5) urethane gels; (6) water based gels; triblock copolymer gels especially suitable for use: (7) SEBS gels; examples include: (a) Kraton G 1651, G 1654X gels; (b) Kraton G 4600 gels; (c) Kraton G 4609 gels; other less suitable SEBS oil gels: examples include: (d) Tuftec H 1051 gels; (e) Tuftec H 1041 gels; (f) Tuftec H 1052 gels. Gels made from blends (polyblends) of (a)–(f) with other polymers and copolymers include: (8) SEBS-SBS gels; (9) SEBS-SIS gels; (10) SEBS-(SEP) gels; (11) SEBS-(SB)n gels; (12) SEBS-(SEB)n gels; (13) SEBS-(SEP)n gels; (14) SEBS-(SI)n gels; (15) SEBS-(SI) multiarm gels; (16) SEBS-branched copolymers gels; (17) SEBS-star shaped copolymer gels; gels made from blends of (a)–(f) with other homopolymers include: (18) SEBS/polystrene gels; (19) SEBS/polybutylene gels; (20) SEBS/polyethylene gels; (21) SEBS/polypropoylene gels; (22) inner layer/outer layer gels; triple-layer gels: (23) urethane-silicone-SEBS layered gels. Other suitable thermoplastic elastomers in blends suitable for making gels include SEP/SEBS oil gels (24), SEP/SEPS oil gels (25), SEP/SEPS/SEB oil gels (26), SEPS/SEBS/SEP oil gels (27), etc.

The following commercial elastomers can be formed with oil and in combination with other polymers (a)–(c), (d)–(f), and/or (8)–(20) into suitable gels for use in making the bodies 2 of the invention: Shell Kratons D1101 (SBS), D1102 (SBS), D1107 (SIS), D1111 (SIS), D1112 (SIS), D1113X (SIS), D1114X (SIS), D1116 (SB)$_n$ branched, D1117 (SIS), D1118X (SB) diblock, D1122X (SB)$_n$ braanched, D1125X ((SIS), D1133X (SBS)$_n$ D1135X (SB)$_n$ branched, D1184 (SB), branched, D1188X (SB)$_n$ branched, D1300X (SI)$_n$, D1320X (SI)$_n$ multi-ann, D4122 (SBS), D4141 (SBS), D4158 (SB)$_n$ branched, D4240 (SB)$_n$ branched, G1650 (SEBS), G1652 (SEBS), G1657 (SEBS), G1701X (SEP) diblock, G1702X (SEP) diblock, G1726X (SEBS), G1750X (EP)$_n$ multi-arm, G1765X (EP)$_n$ multi-arm, FG1901X (SEBS), FG1921X (SEBS), D2103, D2109, D2122X, D3202, D3204, D3226, D5298, D5999X, D7340, G1654X, G2701, G2703, G2705, G1706, G2721X, G7155, G7430, G7450, G7523X, G7528X, G7680, G7705, G7702X, G7720, G7722X, G7820, G7821X, G7827, G7890X, G7940; Kumray's (SEP), (SEPS) or (SEB/EPS) Nos. 1001 (SEP), 2002 (SEPS), 2063 (SEPS), 2023 (SEPS), 2043 (SEPS), 2063 (SEPS), 2005 (SEPS), 2006 (SEPS), 2050 (SEPS), 2103 (SEPS), 2104 (SEPS), 2105 (SEPS), and 4055 (SEB/EPS) (styrene-ethylene-butylene/ethylene-propylene-styrene) block polymer made from hydrogenated styrene isoprene/butadiene styrene block copolymer or more specifically made from hydrogenated styrene block polymer with 2-methyl-1,3-butadiene and 1,3-butadiene. Where the ethylene (E) of the ethylene-butylene (EB) segment of the midblock (EB/EP) of the (SEB/EPS) block polymer is substantially greater than butylene (B) so as to exhibit ethylene crystallinity, (SEB/EPS) may be denoted as (SE/EPS) or denoted as (SEEPS) block polymer for sake of simplicity.

The most preferred gels forming the bodies 2 of the invention comprise a high viscosity triblock copolymers which have the more general configuration A-B-A wherein each A is a crystalline polymer end block segment of polystyrene; and B is a elastomeric polymer center block segment of poly(ethylene-butylene). The poly(ethylene-butylene) and polystyrene portions are incompatible and form a two-phase system consisting of sub-micron domains of glassy polystyrene interconnected by flexible poly(ethylene-butylene) chains. These domains serve to crosslink and reinforce the structure. This physical elastomeric network structure is reversible, and heating the polymer above the softening point of polystyrene temporarily disrupt the structure, which can be restored by lowering the temperature. Most recent reviews of triblock copolymers are found in the "ENCYCLOPEDIA OF POLYMER SCIENCE AND ENGINEERING", Volume 2 and 5, 1987–1988; "Thermoplastic Elastomers", MODERN PLASTIC ENCYCLOPEDIA, 1989; and Walker, B. M., Ed,. et al., HANDBOOK OF THERMOPLASTIC ELASTOMERS, Van Nostrand Reinhold Co., 2nd Edition, 1988. There publications are incorporated herein by reference).

More specifically, the especially suitable gels for use in the the present invention may be prepared in accordance with the methods disclosed in U.S. Pat. Nos. 4,369,284; 4,618,213; 5,239,723; 5,262,468 and other related applications and patents referred to above which are herein incorporated by reference.

The especially suitable gels can be prepared by melt blending an admixture comprising: (A) 100 parts by weight of a high viscosity triblock copolymer of the general configuration poly(styrene-ethylene-butylene-styrene) (herein referred to as "SEBS") where said triblock copolymer is characterized as having a Brookfield Viscosity of a 20 weight percent solids solution of said triblock copolymer in toluene at 25° C. of about 1,800 cps and higher. (B) from about 200 to about 1,300 parts by weight of an plasticizing oil.

Less typically, the Brookfield viscosity values of (A) can range from about 1,800 cps to about 30,000 cps or higher. The proportion of hydrocarbon plasticizing oil in (B) is more preferably from about 250 to about 1,200 parts per 100 parts of the triblock copolymer.

The high viscosity triblock copolymer of the invention can have a broad range of styrene end block to ethylene and butylene center block ratio of approximately about 20:80 or less to about 40:60 or higher. Examples of high viscosity triblock copolymers that can be utilized to achieve one or more of the novel properties of the present invention are styrene-ethylene-butylene-styrene block copolymers (SEBS) available from Shell Chemical Company and Pecten Chemical Company (divisions of Shell Oil Company) under trade designations Kraton G 1651, Kraton G 1654X, Kraton G 4600, Kraton G 4609 and the like. Other grades of (SEBS) polymers can also be utilized in the present invention provided such SEBS polymers exhibits the required high viscosity. Such SEBS polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C.

The styrene to ethylene and butylene weight ratios for these Shell designated polymers can have a low range of 20:80 or less. Although the typical ratio values for Kraton G 1651, 4600, and 4609 are approximately about 33:67 and for Kraton G 1855X approximately about 27:73, Kraton G 1654X (a lower molecular weight version of Kraton G 1651 with somewhat lower physical properties such as lower solution and melt viscosity) is approximately about 31:69, these ratios can vary broadly from the typical product specification values.

The styrene to ethylene and butylene weight ratio of SEBS useful in forming the bodies 2 can range from lower than about 20:80 to above about 40:60. More specifically, the values can be 19:81, 20:80, 21:79. 22:78. 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 and etc. Other ratio values of less than 19:81 or higher than 51:49 are also possible. Shell Technical Bulletin SC:1393-92 gives solution viscosity as measured with a Brookfield model RVT viscometer at 25° C. for Kraton G 1654X at 10% weight in toluene of approximately 400 cps and at 15% weight in toluene of approximately 5,600 cps. Broadly, the styrene end block to ethylene and butylene center block ratio of the triblock copolymers of the invention is about 20:80 to about 40:60, less broadly about 31:69 to about 40:60, preferably about 32:68 to about 38:62, more preferably about 32:68 to about 36:64, particularly more preferably about 32:68 to about 34:66, especially more preferably about 33:67 to about 36:64, and most preferably about 33:67. In accordance with the present invention, triblock copolymers such as Kraton G 1654X having ratios of 31:69 or higher can be used and do exhibit some very similar physical properties in many respects to Kraton G 1651 while Kraton G 1654X with ratios below 31:69 may also be use, but they are less preferred due to their decrease in the desirable properties of the final gel. Various triblock copolymers of the gels forming the humdingers of the invention can be blended so as to produce a blend of varying ratios of triblock copolymers as desired.

Examples of representative commercially oils include Amoco® polybutenes, hydrogenated polybutenes and polybutenes with epoxide functionality at one end of the polybutene polymer: Example of such polybutenes include: L-14 (320 Mn), L-50 (420 Mn), L-100 (460 Mn), H-15 (560 Mn), H-25 (610 Mn), H-35 (660 Mn), H-50 (750 Mn), H-100 (920 Mn), H-300 (1290 Mn), L-14E (27–37 cst@100° F. Viscosity), H-300E (635–690 cst@210° F. Viscosity), Actipol E6 (365 Mn), E16 (973 Mn), E23 (1433 Mn) and the like. Example of various commercially oils include: ARCO Prime (55, 70, 90, 200, 350, 400 and the like), Duraprime and Tufflo oils (6006, 6016, 6016M, 6026, 6036, 6056, 6206, etc), other white mineral oils include: Bayol, Bernol, American, Blandol, Drakeol, Ervol, Gloria, Kaydol, Litetek, Lyondell (Duraprime 55, 70, 90, 200, 350, 400, etc),. Marcol, Parol, Peneteck, Primol, Protol, Sontex, and the like.

Generally, plasticizing oils with average molecular weights less than about 200 and greater than about 700 may also be used (e.g. H-300 (1290 Mn)).

Other polymers and copolymers (in major or minor amounts) can be melt blended with the SEBS as mentioned above without substantially decreasing the desired properties. Such polymers may also be utilized in one or more regions of the bodies 2 of the invention; these include (SBS) styrene-butadiene-styrene block copolymers, (SIS) styrene-isoprene-styrene block copolymers, (low styrene content SEBS) styrene-ethylene-butylene-styrene block copolymers, (SEP) styrene-ethylene-propylene block copolymers, (SEPS) styrene-ethylene-propylene block copolymers, (SB)n styrene-butadiend and (SEB)n, (SEBS)n, (SEP)n, (SI)n styrene-isoprene multi-arm, branched, and star shaped copolymers and the like. Still, other homopolymers can be utilized in minor amounts; these include: polystyrene, polybutylene, polyethylene, polypropylene and the like.

Gels having gel rigidities of from about 100 gram Bloom to about 1,500 gram Bloom and higher are especially advantageous and suitable for forming the bodies 2 of the invention.

As used herein, the term "gel rigidity" in gram Bloom is determined by the gram weight required to depress a gel a distance of 4 mm with a piston having a cross-sectional area of 1 square centimeter at 23° C.

Gels less suitable and less advantageous for use in the present invention include polymer gels, crosslinked polymer gels, and the like. These are found in U.S. Pat. Nos. 4,833,193; 4,709,982; 4,716,183; 4,497,538; 4,509,821; 4,351,913; 4,432,607; 5,149,736; PCT Publications WO88/00603; WO9/305113; and WO91/05014.

Other less suitable gels include high strength silicone gels (e.g., Dow Sylgard gel, etc.), urethane gels, water gels (PVA, PEO), and the like. Such gels are inherently weak and do not make good bodies 2 by themselves; they can not withstand the centrifugal force generated during rotation. Such weak gels can be enclosed by the stronger (high strength gels) more advantageous gels described in the invention.

A gel of about 800 to 1,500 gram Bloom and higher are especially suited as a high strength gel 10 (i.e., resistant to the cutting actions of the twisting string 5) for use in surrounding the holes 6 of the bodies (2). Less suitable strength gel 10 are characterized by a gel rigidity of much less than about 800 gram Bloom. bodies 2 of humdinger made with high strength tubes 8 are characterized by a gel rigidity of at least above about 80 gram Bloom. bodies 2 utilizing high strength reinforced interlocking materials are characterized by an outer gel rigidity of at least above about 80 gram Bloom.

Such high strength gels 10 are prepared by decreasing the plasticizing oil content to about 200 to about 600 parts to 100 parts by weight of the high viscosity SEBS. The resulting higher strength gel 10 will have sufficient strength to prevent the holes 6 of the bodies 2 from being cut easily by the strings 5. Less preferred are the gels with rigidities of about 300 to about 1,500 gram Bloom and higher; these are suitable for use as bodies 2 without the additional need for reinforcing, interlocking material 9 or tube 8 to protect the holes 6 against cutting by the twisting string 5. With respect to bodies 2 made from gels having rigidities in the range of about 750 to about 1,500 and higher, these are especially preferred for use as humdingers of the invention.

The gel utilized for the bodies 2 can also contain useful amounts of conventionally employed additives such as stabilizers, antioxidants, antiblocking agents, colorants, fragrances, flame retardants, other polymers in minor amounts and the like to an extend not affecting or substantially decreasing the desired properties of the present invention.

Additives useful in the gel of the present invention include: tetrakis[methylene 3,-(3'5'-di-tertbutyl-4"-hydroxyphenyl) propionate] methane, octadecyl 3-(3",5"-di-tert-butyl-4"-hydroxyphenyl) propionate, distearyl-pentaerythritol-diproprionate, thiodiethylene bis-(3,5-ter-butyl-4-hydroxy) hydrocinnamate, (1,3,5-trimethyl-2,4,6-tris[3,5-di-tert-butyl-4-hydroxybenzyl] benzene), 4,4"-methylenebis(2,6-di-tert-butylphenol), steraric acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, waxes (e.g. polyethylene, polypropylene, microcrystalline, carnauba, paraffin, montan, candelilla, beeswax, ozokerite, ceresine, and the like). The gel can also contain metallic pigments (aluminum and brass flakes), $TiO_2$, mica, fluorescent dyes and pigments, phosphorescent pigments, aluminatrihydrate, antimony oxide, iron oxides ($Fe_3O_4$, —$Fe_2O_3$, etc.), iron cobalt oxides, chromium dioxide, iron, barium ferrite, strontium ferrite and other magnetic particle materials, molybdenum, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite and the like. The report of the committee on Magnetic Materials, Publication NMAB-426, National Academy Press (1985) is incorporated herein by reference.

The gels forming the humdingers of the invention can also contain gases as an additive, i.e. the gel can be foamed. Foam is herein defined as tightly or loosely packing aggregation of gas bubbles, separated from each other by thin or thick layers of gel. Many types of foamed gels (from ultra high density to ultra low density) can be produced as desired by (i) adding gas to the molten gel during processing, and (ii) producing gas in the molten gel during processing. Gas can be added by whipping a gas into the molten gel before it cools or introduce a gas into the molten gel and then expand or reduce the size of the gas bubbles by reducing the pressure to reduce the bubbles size or applying high pressure to expand the bubbles size. In this regard, inert gases such as Carbon dioxide, Nitrogen, Helium, Neon, Argon, Krypton, Xenon and Radon are suitable. Air can also be used. Gas can be produced in the molten gel by adding one or more of a "blowing agent" to the. Useful blowing agents include dinitroso compounds, such as dinitroso pentamethylene-tetramine, azodicarbonamide, 4,4'oxybis (benzenesulfonyl) hydrazine, 5-phenyltetrazole, p-toluenesulfonyl semicarbazide, sulfonyl hydrazide, such as benzene sulfonylhydrazide. Water can be used as a "blowing agent" to 1 produce varying density of foam gels; water used to advantage can be in the form of mist, droplets, steam, and hot or cold water. The density of the foam gels can vary from less than 1.00 kilograms per cubic meter to near the solid gel density.

Although the materials forming soft solid bodies 2 may be more shear resistant, the same materials when made into a foam become much less shear resistant. In general, foams that can be cut by a first, second or higher order twisting string 5 are made of open-cell and close-cell foams (without gel) which include: Neoprene, polysulfide, silicone, polyvinyl chloride, chorosulfonated polyethylene, fluorelastomers, ethylene-propylene, polyamides, polyimides, polyesters, polyisocyanurates, polyisocyanates, polyurethanes, poly (vinyl alcohol), polycarbonate, PPO, polysulfone, polyethylene, polystyrene, polypropylene, etc. Open-cell and close-cell foams are described in "Expanded Plastics and Related Products", Chemical Technology Review No. 221, Noyes Data Corp., 1983, and "Applied Polymer Science", Organic Coatings and Plastic Chemistry, 1975; and Foamed Plastics, Chapter 20, 1985. These publications are incorporated herein by reference. Moreover, other low strength elastic materials such as: very soft, uncured2 rubber gum (natural rubber, butyl rubber, Polyisoprene, polybutadiene, etc.), soft cure rubber (silicone rubber, nitrile, Hypalon, Vistanex, etc.), polymeric foams, plastic foam (polyethylene, polypropylene, polystyrene, polycarbonate, etc.), natural rubber foams and synthetic rubber foams can also be easily cut by a first or second order (shearing) of a twisting string 5. While gels may be very soft and have a low strength strength, for the purpose of this invention, any material (gels, foam gels, soft uncured rubbers, soft cure rubbers, soft rubber foams, plastic foams and the like) that can be cut by the shearing force of a first or second order twisting string 5 can be used as spinning bodies (2). The teaching of the present invention make it possible to spin any weak, soft, and low strength body 2 suspended on a high shear (first, second, or higher order) twisting string 5. Such low strength bodies can be modified in the same way as the gel bodies 2 of the invention to make them suitable as bodies 2 for high speed string 5 spinning toys.

For example, typical flexible urethane foam may have a tensile strength of 5, 10, 14, 18 psi or higher and a tear strength of from less than 2.2 pound per inch to 5 pound per inch and higher. Such foam material can be cut by a first or second order twisting string 5.

In the operation of the humdingers of the invention, the string's 5 twisting action imparts rotation to the gel body 2 so as to elongate the gel body 2 during rotation. The elongated gel body 2 will reach a maximum elongation due to centrifugal force of 50% or more. Elongations of 100%, 200%, 300%, 400%, 500%, 600%, 700% and higher are possible depending on the amount of tension of the pull of the humdinger's strings 5. Gel bodies 2 of of the invention can be designed to withstand elongations higher than 1,000% which can occur at extreme high rates of rotation of 500 r.p.m. and higher. Spinning rates can span from a low of 10 r.p.m. to a high of over 1,000 r.p.m. Spinning rates of 50, 100, 150, 200, 25, 300, 350, 400, 500, 600, 700, 800, 900, 1,000, 1,200, 1,400 r.p.m. values are routinely achieved.

The operation of the humdingers of the invention can be ready observed under strobe light. The number of revolutions per minute may be counted in this way. The changes in radius can be measured. The change in gel body 2 shape can be observed and measured. The centrifugal force acting on the rotating gel body 2 can be likewise determined at any instant of time, at any instant rate of rotation, at any instant change in gel body 2 shape. The perpendicular-axis elongation effect of the gel body 2 can be view under strobe light; its regions of deformation and redistribution of mass can be viewed, measured and ready determined by ruled grid markings on the gel body (2).

When operating the humdingers of the invention, it is best to hold the looped ends of the strings 5 and adjusted the strings 5 to suspend parallel with respect to each other. The end loops are held loose to allow the strings 5 to droop slightly in the middle. This will cause the body 2 (with tube 8 inserts) to slide towards the midpoint of the strings 5. In order to start the body 2 spinning, the body 2 is twirled several times, then followed by a pull of the end loops in opposite directions in a short, gentle, but firm pulling (non-jerking) action. The strings 5 are relaxed as the strings 5 begin their twisting motion in one direction. As the body 2 nears the end of its rotation cycle in one direction, the strings 5 are given another short and firm pull to unwind the strings 5 and force the body 2 to reverse its spin. The pulling and relaxing actions keep the body 2 spinning. In instances where tubes 8 are used, it is important to make sure the tubes 8 are centered within the body 2 at all times. Should the tubes 8 slide out of the body (2), they should be gently inserted back into the body 2 before resuming spinning. The tubes 8 are positioned inside the body 2 to keep the strings 5 from cutting the soft body 2 during rotation.

The gel bodies may be torqued about a selected axis of rotation by insertion of one or more flexible thin rods in place of the strings.

Moreover, other man made materials or metals in the form of thin metal rods, spring steel wires, piano wires, brass wires, copper wires, synthetic fibers and the like can be use in place of the strings for spinning the bodies of the invention. The bodies may also be casted, molded, or formed in-place with one or more high strength materials strips, rods, or handles serving the same purpose as the strings or rods for rotating the gel bodies.

While certain features of this invention have been described in detail with respect to various embodiments thereof, it will, of course, be apparent that other modifications can be made within the spirit and scope of this invention, and it is not intended to limit the invention to the exact details shown above except insofar as they are defined in the following claims.

What I claim is:

1. A spinning toy, which comprises: a highly elastic gel body made from a gel comprising a hydrogenated poly(styrene isoprene/butadiene styrene) block copolymer, a selected amount of a plasticizer and with or without one or more copolymer selected from poly(styrene-ethylene-butylene-styrene), poly(styrene-ethylene-propylene-styrene), poly(styrene-butadiene-styrene) poly(styrene-isoprene-styrene), poly(styrene-butadiene)n and polymer selected from poly(styrene-isoprene)n, polystyrene, polybutylene, polyethylene, and polypropylene, wherein said copolymer is a multi-arm, branched, or a star shaped copolymer; said gel body having at least two holes at a selected distance apart and extending through said body along a selected axis of rotation, said body suspended by a selected length of a string(s) having ends, said string formed in a loop through said holes with said ends tied together to provide for alternatively clockwise and counterclockwise rotation of said body by the twisting and untwisting of said string, said body being deformed and elongated by the action of centrifugal force of rotation of said body, and said body having sufficient strengths to withstand the centrifugal force of rotation and shearing force of the twisting and untwisting of said string generated by a first, a second, a third, or higher order dynamic twisting of said string during spinning of said gel body at an elongation of 50% or greater.

2. A rotating toy, comprising:
   (a) an elastic solid gel body made from a gel comprising a hydrogenated poly(styrene isoprene/butadiene styrene) block copolymer, a selected amount of a plasticizer and with or without one or more polymer and copolymer selected from poly(styrene-ethylene-butylene-styrene), poly(styrene-ethylene-propylene-styrene), poly(styrene-butadiene-styrene) poly(styrene-isoprene-styrene), poly(styrene-butadiene)n and poly(styrene-isoprene)n, polystyrene, polybutylene, polyethylene, and polypropylene, wherein said copolymer is a multi-arm, branched, or a star shaped copolymer; said gel body;
   (b) one or more strings threaded through at least two points about a selected axis of rotation of said solid gel body to form a loop; said gel body when subjected to rotation will deform in a highly elastic non-radial manner at an elongation of 50% or greater.

3. A spinning toy, which comprises: a soft, highly elastic gel body made from a gel comprising a hydrogenated poly(styrene isoprene/butadiene styrene) block copolymer, a selected amount of a plasticizer and with or without one or more copolymer selected from poly(styrene-ethylene-butylene-styrene), poly(styrene-ethylene-propylene-styrene), poly(styrene-butadiene-styrene) poly(styrene-isoprene-styrene), poly(styrene-butadiene)n and polymer selected from poly(styrene-isoprene)n, polystyrene, polybutylene, polyethylene, and polypropylene, wherein said copolymer is a multi-arm, branched, or a star shaped copolymer; said gel body having at least two holes at a selected distance apart and extending through said body along a selected axis of rotation, and a selected length of two or more shear resistant tubes inserted into said holes and positioned within said body, said body suspended by a selected length of a string having two ends, said string formed in a loop threaded through said tubes residing within said holes with said ends tied together to provide for alternatively clockwise and counterclockwise rotation of said body by the twisting and untwisting of said string, said body being deformed and elongated by the action of centrifugal force of rotation of said body, and said body having sufficient strengths to withstand the centrifugal force of rotation and said tubes having sufficient strengths to withstand the shearing force of the twisting and untwisting of said string generated by a first, a second, a third, or higher order dynamic twisting of said string during spinning of said gel body at an elongation of 50% or greater.

4. A spinning toy, which comprises: a soft, highly elastic gel body made from a gel comprising one or more linear, multi-arm, branched or star shaped block polymers of the configuration poly(styrene-ethylene-butylene-styrene), poly(styrene-ethylene-propylene-styrene), poly(styrene-ethylene-butylene/ethylene-propylene-styrene), poly(styrene-ethylene/ethylene-propylene-styrene), poly(styrene-ethylene-butylene)$_n$, poly(styrene-ethylene-propylene)$_n$, a selected amount of a plasticizer and with or without one or more copolymer selected from poly(styrene-butadiene-styrene) poly(styrene-isoprene-styrene), poly(styrene-butadiene)n and poly(styrene-isoprene)n, polystyrene, polybutylene, and polymer selected from polyethylene, and polypropylene, wherein said copolymer is a multi-arm, branched, or a star shaped copolymer; said gel body having at least two holes at a selected distance apart and extending through said body along a selected axis of rotation, and a shear resistant means inserted within or surrounding said holes, said body suspended by a selected length of a string(s) having ends, said string formed in a loop threaded through said shear resistant means within or surrounding said holes with said ends tied together to provide for alternatively clockwise and counterclockwise rotation of said body by the twisting and untwisting of said string, said body being deformed and elongated by the action of centrifugal force of rotation of said body, and said body having sufficient strengths to withstand the centrifugal force of rotation and said shear resistant means having sufficient strengths to withstand the shearing force of the twisting and untwisting of said string generated by a first, a second, a third, or higher order dynamic twisting of said string during spinning of said gel body at an elongation of 50% or greater.

5. A spinning toy according to claim 4, wherein said shear resistant means which surround said holes comprises a reinforced interlocking material region.

6. A spinning toy according to claim 4, wherein said shear resistant means which surround said holes comprises a shear resistant gel region, said gel region surrounding said holes having a gel rigidity of at least about 600 gram Bloom.

7. A spinning toy according to claim 4, wherein said shear resistant means inserted within said holes comprises two or more shear resistant tubes.

8. A spinning toy according to claim 1, wherein said hydrogenated poly(styrene isoprene/butadiene styrene) block copolymer is made from a hydrogenated styrene block polymer with 2-methyl-1,3-butadiene and 1,3-butadiene; said gel body having a gel rigidity greater than 500 gram Bloom.

9. A spinning toy according to claims 1,3 or 2 wherein said hydrogenated poly(styrene isoprene/butadiene styrene) block copolymer is of the configuration poly(styrene-ethylene-butylene/ethylene-propylene-styrene); said gel body being deformable by the centrifugal force of rotation generated by a torque being variable by a change in the separation of the distance of said holes of said body during spinning of said gel body at an elongation of 50% or greater.

10. A spinning toy according to claims 1, 3 or 2, wherein said hydrogenated poly(styrene isoprene/butadiene styrene)

block copolymer is of the configuration poly(styrene-ethylene/ethylene-propylene-styrene) and said gel body is deformable in a highly elastic non-radial manner during spinning of said gel body at an elongation of 50% or greater.

11. A spinning toy, which comprises: a gel body made from a gel comprising one or more linear, multi-arm, branched or star shaped block polymers of the configuration poly(styrene-ethylene-butylene-styrene), poly(styrene-ethylene-propylene-styrene), poly(styrene-ethylene-butylene/ethylene-propylene-styrene), poly(styrene-ethylene/ethylene-propylene-styrene), poly(styrene-ethylene-butylene)$_n$, poly(styrene-ethylene-propylene)$_n$, a selected amount of a plasticizer and with or without one or more copolymer selected from poly(styrene-butadiene-styrene) poly(styrene-isoprene-styrene), poly(styrene-butadiene)n and poly(styrene-isoprene)n, and polymer selected from polystyrene, polybutylene, polyethylene, and polypropylene, wherein said copolymer is a multi-arm, branched, or a star shaped copolymer; said gel body having at least two holes at a selected distance apart and extending through said body along a selected axis of rotation, and a selected length of two or more shear resistant tubes inserted into said holes and positioned within said body, said body suspended by a selected length of a string(s) having ends, said string formed in a loop threaded through said tubes residing within said holes with said ends tied together to provide for alternatively clockwise and counterclockwise rotation of said body by the twisting and untwisting of said string, said body being deformed and elongated by the action of centrifugal force of rotation of said body, and said body having sufficient strengths to withstand the centrifugal force of rotation and said tubes having sufficient strengths to withstand the shearing force of the twisting and untwisting of said string generated by a first, a second, a third, or higher order dynamic twisting of said string during spinning of said gel body at an elongation of 50% or greater.

12. A method of rotating a body, which comprises:
  (a) forming an elastic gel body made from a gel comprising one or more linear, multi-arm, branched or star shaped block polymers of the configuration poly(styrene-ethylene-butylene-styrene), poly(styrene-ethylene-propylene-styrene), poly(styrene-ethylene-butylene/ethylene-propylene-styrene), poly(styrene-ethylene/ethylene-propylene-styrene), poly(styrene-ethylene-butylene )$_n$, poly(styrene-ethylene-propylene)$_n$, a selected amount of a plasticizer and with or without one or more polymer and copolymer selected from poly(styrene-butadiene-styrene) poly(styrene-isoprene-styrene), poly(styrene-butadiene)n and poly(styrene-isoprene)n, polystyrene, polybutylene, polyethylene, and polypropylene, wherein said copolymer is a multi-arm, branched, or a star shaped copolymer; said gel body having a selected shape, a selected volume, a selected surface, and at least two holes substantially parallel and approximately equal distance along a selected axis of rotation through said volume of said body; said holes optionally having a shear resistant means inserted within or surrounding said holes;
  (b) treading into said holes of said body a selective length of a string(s) having ends; optionally, said string(s) having two or more holding means for holding said string(s);
  (c) tiding said ends of said string(s) together forming a string loop communicating through said holes of said body;
  (d) suspending said body by said string(s);
  (e) holding said string by said holding means;
  (f) twirling said body about said string(s) followed by
  (g) pulling and relaxing said string(s) so as to cause a continued twisting and untwisting actions of said string loop and the rotation of said gel body thereby deforming said volume of said gel body by the centrifugal force of rotation; said twisting and untwisting actions is capable of generating a first, a second, a third, or higher order dynamic twisting of said string during spinning of said gel body at an elongation of 50% or greater.

13. A rotating string toy, which comprises a variable torque humdinger including:
  (a) a highly elastic solid gel body made from a gel comprising one or more linear, multi-arm, branched or star shaped block polymers of the configuration poly(styrene-ethylene-butylene-styrene), poly(styrene-ethylene-propylene-styrene), poly(styrene-ethylene-butylene/ethylene-propylene-styrene), poly(styrene-ethylene/ethylene-propylene-styrene), poly(styrene-ethylene-butylene)$_n$, poly(styrene-ethylene-propylene)$_n$, a selected amount of a plasticizer and with or without one or more polymer and copolymer selected from poly(styrene-butadiene-styrene) poly(styrene-isoprene-styrene), poly(styrene-butadiene)n and poly(styrene-isoprene)n, polystyrene, polybutylene, polyethylene, and polypropylene, wherein said copolymer is a multi-arm, branched, or a star shaped copolymer; said gel body capable of exhibiting an elongated deformation by the action of centrifugal force of rotation and an equal and opposite action of an elastic force equal to the centrifugal force by said gel body;
  (b) means for applying a torque about a selected axis of rotation of said gel body so as to produce alternate rotation of said gel body about said axis and maintaining rotation of said gel body by said means so as to cause said elongated deformation by the centrifugal force of rotation of said gel body at an elongation of 50% or greater.

14. A rotating toy, comprising:
  (a) a highly elastic solid gel body made from a gel comprising one or more linear, multi-arm, branched or star shaped block polymers of the configuration poly(styrene-ethylene-butylene-styrene), poly(styrene-ethylene-propylene-styrene), poly(styrene-ethylene-butylene/ethylene-propylene-styrene), poly(styrene-ethylene/ethylene-propylene-styrene), poly(styrene-ethylene-butylene)$_n$, poly(styrene-ethylene-propylene)$_n$, a selected amount of a plasticizer and with or without one or more polymer and copolymer selected from poly(styrene-butadiene-styrene) poly(styrene-isoprene-styrene), poly(styrene-butadiene)n and poly(styrene-isoprene)$_n$, polystyrene, polybutylene, polyethylene, and polypropylene, wherein said copolymer is a multi-arm, branched, or a star shaped copolymer; said gel body;
  (b) a string threaded through at least two points about a selected axis of rotation of said gel body to form a loop; optionally, said gel body comprising
  (c) one or more of a shear resistant means through said points about said selected axis of rotation correspondingly surrounding said string threaded through said gel body; said gel body when subjected to rotation will deform in a highly elastic non-radial manner at an elongation of 50% or greater.

15. A rotating toy, comprising:
  (a) an elastic solid gel body made from a gel comprising one or more linear, multi-arm, branched or star shaped block polymers of the configuration poly(styrene-ethylene-butylene-styrene), poly(styrene-ethylene-propylene-styrene), poly(styrene-ethylene-butylene/ethylene-propylene-styrene), poly(styrene-ethylene/ethylene-propylene-styrene), poly(styrene-ethylene-butylene)$_n$, poly(styrene-ethylene-propylene)$_n$, a selected amount of a plasticizer and with or without one or more polymer and copolymer selected from poly(styrene-butadiene-styrene) poly(styrene-isoprene-styrene), poly(styrene-butadiene)n and poly(styrene-isoprene)n, polystyrene, polybutylene, polyethylene, and polypropylene, wherein said copolymer is a multi-arm, branched, or a star shaped copolymer; said gel body;

(b) a string threaded through at least two points about a selected axis of rotation of said gel body to form a loop; said gel body when subjected to rotation will deform in a highly elastic non-radial manner at an elongation of 50% or greater.

* * * * *